US00PP10686P

United States Patent [19]

Ackerman et al.

[11] Patent Number: Plant 10,686

[45] Date of Patent: Nov. 17, 1998

[54] STRAWBERRY PLANT NAMED 'PS-1269'

[75] Inventors: Stephen M. Ackerman, Salinas; Michael D. Nelson; Steven D. Nelson, both of Watsonville, all of Calif.

[73] Assignees: Plant Sciences, Inc.; Berry R & D, Inc., both of Watsonville, Calif.

[21] Appl. No.: 871,778

[22] Filed: Jun. 9, 1997

[51] Int. Cl.[6] ..... A01H 5/00

[52] U.S. Cl. ..... Plt./48

[58] Field of Search ..... Plt./48, 49

*Primary Examiner*—James R. Feyrer

*Attorney, Agent, or Firm*—Foley & Lardner

[57] ABSTRACT

This invention relates to a new and distinct winter-planted short-day-type variety of strawberry designated 'PS-1269'. This new variety is primarily adapted to the growing conditions of the central coast of California with the ability to remain in fruit production from April through November. It is particularly characterized by its early fruit production, large-sized berries and fruit and flowers visible above the canopy of the plant much of the year. The fruit is very attractive and glossy when just picked with a tendency to become dull after cold storage. The plant is strong and moderately vigorous when provided with optimum chilling and cold storage prior to planting but may become small and compact when chilling and/or cold storage is lacking. The foliage has a strong tendency to cup upward at the margins. This cupping action may in part be due to its susceptibility to powdery mildew although the foliage will still cup when powdery mildew is not present. The cuppling may also become more extreme when the plants become stressed due to lack of chilling.

3 Drawing Sheets

BACKGROUND OF THE INVENTION

The present invention relates to a new and distinct short-day-type strawberry variety designated as 'PS-1269'. This new variety is a result of an open-pollinated seedling of unknown parentage. The variety is botanically known as *F.* × *ananassa* Duch.

SUMMARY OF THE INVENTION

The new variety of strawberry designated 'PS-1269' resulted from a breeding program jointly sponsored by Plant Sciences, Inc. and Berry R & D, Inc., both of Watsonville, Calif., having the objective of developing new and distinct strawberry varieties. The resulting seedling was asexually propagated by stolons in a nursery located in Lassen County, Calif., and was subsequently selected from a controlled breeding plot in Watsonville, Calif. in 1992. After its selection, the new variety was further asexually propagated in Lassen County, Calif, by stolons and extensively tested over the next several years in fruiting fields in Watsnville and Salinas, Calif. Propagation and reproduction trials have demonstrated that the combination of traits disclosed herein as characterizing the new variety are fixed and remain true-to-type through successive generations of asexual reproduction.

BRIEF DESCRIPTION OF THE PHOTOGRAPHS AND FIGURES

The accompanying color photographs show typical specimens of the new variety at various stages of development, the colors in the photographs are as true as it is possible to make in color reproductions. Phenotypic expressions of particular traits may vary with differences in growth, environmental and cultural conditions without any change in the genotype of the variety.

Sheet 1 shows typical plant growth, flowering and fruiting characteristics in mid-July 1996. The photograph illustrates the plant vigor, visibility of the flowers above the canopy of the plant, upward cupping of the foliage, and upright growth habit.

Sheet 2 shows a close-up of maturing fruit in mid-July 1996.

Finally, Sheet 3 shows a close-up view of fruit harvested in mid-August 1996 and packed in a standard twelve dry pint crate.

DETAILED BOTANICAL DESCRIPTION OF THE NEW VARIETY

'PS-1269' is primarily adapted to the climate and growing conditions of the central coast of California. This region provides the necessary winter temperatures required for it to produce a strong vigorous plant and to remain in fruit production from April through November. The nearby Pacific Ocean provides the needed humidity and cool temperatures to maintain fruit quality during the summer production months.

'PS-1269' is a moderately vigorous plant when provided with optimum chilling in nursery propagation fields prior to being dug and artificial cold storage prior to being planted. The plant of the new variety tends to be smaller and less vigorous than 'PS-1269' claimed in U.S. Plant Pat. No. 9,903, 'PS-1269' generally produces fewer runners per plant in the fruiting fields than 'PS-118' claimed in U.S. Plant Pat. No. 8,205. The leaves of 'PS-1269' are smaller and more rounded in shape than 'PS-592'. The foliage of the new variety is lighter in color than both 'PS 118' and 'PS-592'. The leaves of 'PS-1269' have a similar number of serrations compared to both 'PS-118' and 'PS-592', but the serrations of 'PS-1269' are shallower than the other varieties. The foliage has a strong tendency to cup upward at the margins. This cupping action may in part be due to its susceptibility to powdery mildew although the foliage will still cup when powdery mildew is not present. This characteristic cupping distinguishes 'PS-1269' from both 'PS-118' and 'PS-592'. Petioles are thinner in diameter than 'PS-592' while the petiolules are longer in length than both 'PS-118' and 'PS-592'. Table 5 compares foliage characteristics of 'PS-1269', 'PS-118' and 'PS-592'.

'PS-1269' is capable of long season fruit production with fruit of excellent size and flavor when provided with optimum chilling in nursery propagation fields and artificial cold storage prior to being planted. Fruit production begins as early as late March to early April in Salinas, Calif., and may continue cropping into November if rains and cold tempeatures do not prevent the harvest. April production is earlier and heavier than 'PS-118' and similar to 'PS-592'. 'PS-1269' season average fruit size is larger than 'PS-118' but similar to 'PS-592'. The total seasonal yield for 'PS-1269' is less than 'PS-592' and greater than 'PS-118'. (See Table 1).

At the time of harvest the fruit of 'PS-1269' is glossy and very attractive. After cold storage the skin firmness of 'PS-1269' remains superior to 'PS-592' and similar to 'PS-118'. 'PS-592' and 'PS-118' have more noticeable gloss and better overall appearance than 'PS-1269' after storage. See Table 3 for fruit quality performance ratings. The primary berries of 'PS-1269' tend to occasionally produce seedy tipped fruit during much of the season, while secondary and tertiary berries tend to be free of seedy tips. In comparison 'PS-118' tends to produce seedy tipped fruit on all stages during much of the year, while 'PS-592' lacks seedy tips. The seeds of 'PS-1269' are typically held even with the surface of the fruit, in contrast, 'PS-118' tends to have a seedy surface with its seeds positioned more exerted from the surface. The fruit color of 'PS-1269' is lighter than 'PS-118' and darker than 'PS-592'. The fruit of 'PS-1269' is more uniformly conic in shape than 'PS-118' with the exception of the primaries which tend to have more creased berries than 'PS-118'. The sepals of 'PS 1269' are large and more overlapping than both 'PS-118' and 'PS-592'. Flavor panels have rated 'PS-1269' as having better flavor than both 'PS-118' and 'PS-592', (see Table 4).

The total inflorescence length of 'PS-1269' is similar in length to both 'PS-118' and 'PS-592' especially at the time of this evaluation. The primary peduncle during June is slightly shorter in length and larger in diameter than 'PS-118' yet similar to 'PS-592'. The primary pedicel is longer in length and larger in diameter than 'PS-118'. Flowers are noticeably more visible above the canopy as compared to 'PS-592'. See Table 6 for inflorescence characteristics.

SPECIFIC DESCRIPTION OF THE NEW VARIETY

The following is a detailed description of 'PS-1269', including the variety's morphological, electrophoretic, pest and disease reaction characteristics. This detailed description is based on observations taken during June of 1996 in Salinas, Calif. Some characteristics were rated at different times and in that instance, the date of the evaluation will be listed. These measurements and ratings were made from plants dug from a high-elevation nursery located in Lassen County, Calif. in October 1995 and planted in Salinas, Calif. in November 1995. The expression of certain characteristics of the new variety may vary in detail, depending upon variations in environmental factors, including weather (temperature, humidity and light intensity), day length, soil type and location, without any change in genotype. 'PS-1269' has not been observed under all possible environmental conditions. Color terminology follows the Munsell Book of Colors, Munsell Color, Baltimore, Md. (1976).

Fruit Characteristics

'PS-1269' fruit, fruit production and runner production (fruiting field) characteristics are compared to those of 'PS-118' and 'PS-592'.

TABLE 1

1996 market fruit yield, fruit size and runner production characteristics from plants harvested from April through November of 1996 of 'PS-1269' plants from a high elevation nursery (McArthur, California) dug October 15, 1995 and planted November 14, 1995 and compared with standard cultivars in Salinas, California.

| CULTIVAR | APRIL YIELD GM/PL | TOTAL YIELD GM/PL | AVERAGE FRUIT SIZE G/FR | AVERAGE RUNNERS/PL |
|---|---|---|---|---|
| 'PS-1269' | 177 | 1443 | 27.2 | 0.3 |
| 'PS-118'* | 56 | 1299 | 23.0 | 0.7 |
| 'PS-592'** | 195 | 2188 | 25.7 | 0.0 |

*'PS-118' dug October 17, 1995 and planted November 14, 1995 from McArthur, California.
**'PS-592' dug October 15, 1995 and planted November 14, 1995 from McArthur, California.

TABLE 2

Comparison of primary fruit characteristics of 'PS-1269', 'PS-118' and 'PS-592' from Salinas, California, June 19, 1996.

| CHARACTER | 'PS-1269' | 'PS-118' | 'PS-592' |
|---|---|---|---|
| Munsell Color | 7.5R 4/10 to 7.5R 3/10 | 7.5R 3/10 to 7.5R 2/8 | 7.5R 3/12 to 7.5R 4/12 |
| Fruit Length mean (cm) | 5.0 | 4.2 | 5.6 |
| Fruit Width mean (cm)* | 4.5 | 4.3 | 4.4 |
| Calyx Diameter mean (cm) | 5.1 | 5.4 | 5.9 |
| Sepals/Berry mean | 16.3 | 15.2 | 13.9 |
| % Soluble Solids** | 8.5 | 7.7 | 8.1 |

*Width is measured across the widest part of the berry, typically across the shoulders.
**Results are an average of 6 evaluations from fruit harvested from Salinas, California after being held for 5–6 days in cold storage.

TABLE 3

Comparison of 1995–1996 fruit quality characteristics of 'PS-1269', 'PS-118' and 'PS-592' from Salinas, California.*

| CHARACTER | 'PS-1269' | 'PS-118' | 'PS-592' |
|---|---|---|---|
| Skin Firmness | 8.4 | 8.2 | 7.5 |
| Fruit Appearance | 6.8 | 7.6 | 8.2 |
| Fruit Gloss | 6.2 | 8.5 | 7.9 |

*Results are averaged from 2 years of replicated holding tests performed from April through October 1995 and 1996. Ratings are based on a scale from 1–10; the higher the rating, the stronger the skin and the more attractive and glossy the berry.

TABLE 4

Comparison of 1996 flavor test summary of 'PS-1269', 'PS-118' and 'PS-592'.*

| CHARACTER | 'PS-1269' | 'PS-118' | 'PS-592' |
|---|---|---|---|
| Rating | 3.4 | 2.9 | 3.0 |

*Results are an average of 7 flavor tests from fruit harvested from Salinas, California after being held for 5–6 days in cold storage. Ratings are based on scores of 1–5 with 5 being the best.

The fruit is large in size, characteristically conic in shape. Primary berries are typically longer than wide with a tendency to develop wedge-shaped fruit and longitudinal creases. The secondary and tertiary berries are also typically longer than wide and mostly symmetrically conic in shape. The fruit surface is medium red in color with a light colored flesh and core. See Table 2 for fruit comparison characteristics. The fruit surface is smooth with the seeds held flush to the surface. The seeds are yellow and only darken slightly with prolonged exposure to direct sunlight. The seeds are spaced evenly over the surface of the berry with seedy tipped fruit only occurring typically on the primaries and/or under adverse, (rainy and/or windy) weather conditions. The flesh is very firm with good texture and excellent flavor. At the time of harvest the fruit is glossy and very attractive, but after cold storage the fruit may become dull with picking marks and bruising becoming more visible. See Tables 3 and 4, respectively, for fruit quality and flavor characteristics. The calyx of the primary berry is medium in diameter with large overlapping sepals. The calyx attaches slightly below the base of the fruit with necked fruit seldom occurring. The sepals are large and broad, elliptical to ovate in shape with acute apexes. Primary berry sepals are serrated with secondary and tertiary berries only occasionally serrated. Fruit skin is moderately susceptible to cracking due to rain. Pollination is sometimes affected by rain and/or wind resulting in seedy tipped fruit and malformed berries.

Plant Characteristics

The plant of 'PS-1269' is medium in size with multiple crowns producing few runners if given the proper chilling levels prior to being dug, and artificially, prior to being planted. Excessive chilling will result in an over-vigorous plant with a reduction in total fruit yield and increased runner production. Although the plant may become over-vigorous and dense if provided with excessive field chilling and/or artificial cold storage prior to being planted, it generally does not become too large unless chilling and/or storage levels greatly exceed acceptable limits. If chilling is lacking, the plant will remain small and compact. The foliage grows upright on moderately long thin petioles with a tendency to cup upward at the margins. The plant canopy has a relatively medium-light colored appearance.

Foliage Characteristics 'PS-1269' foliage characteristics are compared to those of 'PS-118' and 'PS-592'.

TABLE 5

Comparison of leaf characteristics of 'PS-1269', 'PS-118' and 'PS-592' from Salinas, California, June 19, 1995.

| CHARACTER | 'PS-1269' | 'PS-118' | 'PS-592' |
|---|---|---|---|
| Munsell leaf color (upper Surface) | 7.5GY 3/4 to 7.5GY 3/6 | 7.5GY 3/4 | 7.5GY 4/4 |
| Terminal leaflet Length mean (cm) | 8.8 | 9.5 | 11.2 |
| Terminal leaflet Width mean (cm) | 9.0 | 8.9 | 8.9 |
| Terminal leaflet ratio (L/W) | 0.98 | 1.06 | 1.26 |
| Petiole length mean (cm) | 19.8 | 22.5 | 20.9 |
| Petiole width mean (mm) | 4.0 | 4.0 | 5.0 |
| Petiolule length mean (mm) | 15.8 | 13.5 | 10.3 |
| Serrations/leaf | 19.8 | 18.2 | 18.6 |
| Serration depth mean (mm) | 4.7 | 6.2 | 6.2 |

The foliage of 'PS-1269' is medium in size, light to moderately glossy, medium-light in color and moderately rugose with a strong tendency to cup upward at the margins. This cupping action may in part be due to its susceptibility to powdery mildew although the foliage will cup when powdery mildew is not present. The cupping may also become more extreme when the plants become stressed due to lack of chilling. The terminal leaflet is tpically as wide as it is long as described by the length/width ratio. See Table 5 for foliage comparison characteristics. Leaflets have a moderate number of relatively shallow serrations at the margins, with moderately acute apexes. These serrations typically occur singly, with doubles commonly occurring at the apex of the leaf. Petioles are considered medium in length and thin in diameter with bract leaflets commonly occurring singly or in pairs. Petiolules are also considered long. Pubescene on the petioles grow irregularly perpendicular to the petiole and irregularly parallel to the upper and lower leaf surface.

Flowers and Inflorescences

'PS- 1269' inflorescence characteristics are compared to those of 'PS-118' and 'PS-592'.

TABLE 6

Comparison of inflorescence characteristics of 'PS-1269', 'PS-118' and 'PS-592' from Salinas, California, June 19, 1996.

| CHARACTER | 'PS-1269' | 'PS-118' | 'PS-592' |
|---|---|---|---|
| Inflorescence Length mean (cm) | 34.6 | 32.2 | 32.9 |
| Primary Peduncle Length mean (cm) | 16.4 | 18.8 | 15.2 |
| Primary Peduncle Width mean (mm) | 5.7 | 4.3 | 5.8 |
| Primary Pedicel Length mean (cm) | 7.2 | 5.6 | 6.6 |
| Primary Pedicel Width mean (mm) | 3.5 | 2.5 | 3.4 |

The inflorescences of 'PS-1269' are long, extending the flowers and fruit beyond the foliage during much of the season. The inflorescence remains erect and visible above the canopy of the plant much of the year until the weight of the ripening fruit causes them to fall to the sides of the bed. The primary peduncle is considered medium in length and large in diameter especially at the time of the evaluation. The pedicel holding the primary berry is considered medium to long in length and large in diameter, and may originate singly from the apex of the primary peduncle or from one of the secondary peduncles. Secondary and tertiary berries are borne on pedicels arising from secondary peduncle apexes. See Table 6 for inflorescence comparison characteristics. Flowers are large in size and readily visible above the canopy of the plant during much of the year.

Anthers produce ample pollen for good pollination except on the very large primaries and during rainy and windy periods when seedy tipped and malformed berries may occur. Flowers produce an average of 5 to 8 obovate-shaped petals per flower. Typically a single large bract leaf is borne on a petiole which originates at the primary peduncle apex alongside the base of one of the secondary peduncles. Bract leaves may also occur in pairs and at the apex of secondary peduncles. Pubescence occurs on all peduncles and pedicels, growing irregularly perpendicular to all surfaces.

Isozymes in Leaf Extract

'PS-1269' isozyme banding characteristics are compared to those of 'PS-118' and 'PS-592'.

TABLE 7

'PS-1269' Isozyme banding patterns compared to 'PS-118' and 'PS-592'.

| CULTIVAR | PGI | PGM |
|---|---|---|
| 'PS-1269' | A2 | C2 |
| 'PS-118' | A7 | C4 |
| 'PS-592' | A8 | C2 |

Studies of protein polymorphism in strawberry by the starch gel electrophoresis method were conducted at Plant Sciences, Inc. to characterize this newly developed variety and distinguish it from similar appearing varieties. See Table 7 for isozyme banding patterns of 'PS-1269', compared to 'PS-118' and 'PS-592'.

Isozymes were extracted from young leaves and characterized, using starch gel electrophoresis techniques. The following isozymes were characterized: phosphoglucoisomerase (PGI: EC 5.3.1.9) and phosphoglucomutase (PGM: EC 2.7.5.1).

The testing used both field and greenhouse grown plant material, all grown in Watsonville, Calif. Newly mature leaves (0.5 g fresh weight) from the growing crowns were used. Samples were collected in the morning, held at 4C and analyzed within six hours.

The tissue preparations, extraction and staining are as reported in S. Arulsekar and D. E. Parfitt, "Isozyme Analysis Procedures for Stone Fruits, Almond, Grape, Walnut, Pistachio, and Fig", HortScience 21(4): 928–933.

Following electrophoresis, the gel was sliced and stained for each enzyme system. Banding patterns were interpreted as they developed, and gel slices were fixed in 50% glycerol. The banding pattern codes shown in Table 7 are those of Bringhurst et al. (1981).

In addition, a series of precise molecular markers have been determined for this new variety for unique identification.

Pest Reactions

The new variety may not be resistant to any of the known insects, diseases or viruses common in California. It is known to be moderately susceptible to grey fruit mold, angular leafspot and highly susceptible to powdery mildew. The susceptibility of the new variety to any of the virus complexes of California, has not been determined.

We claim:

1. A new and distinct strawberry variety designated 'PS-1269', as herein described and illustrated.

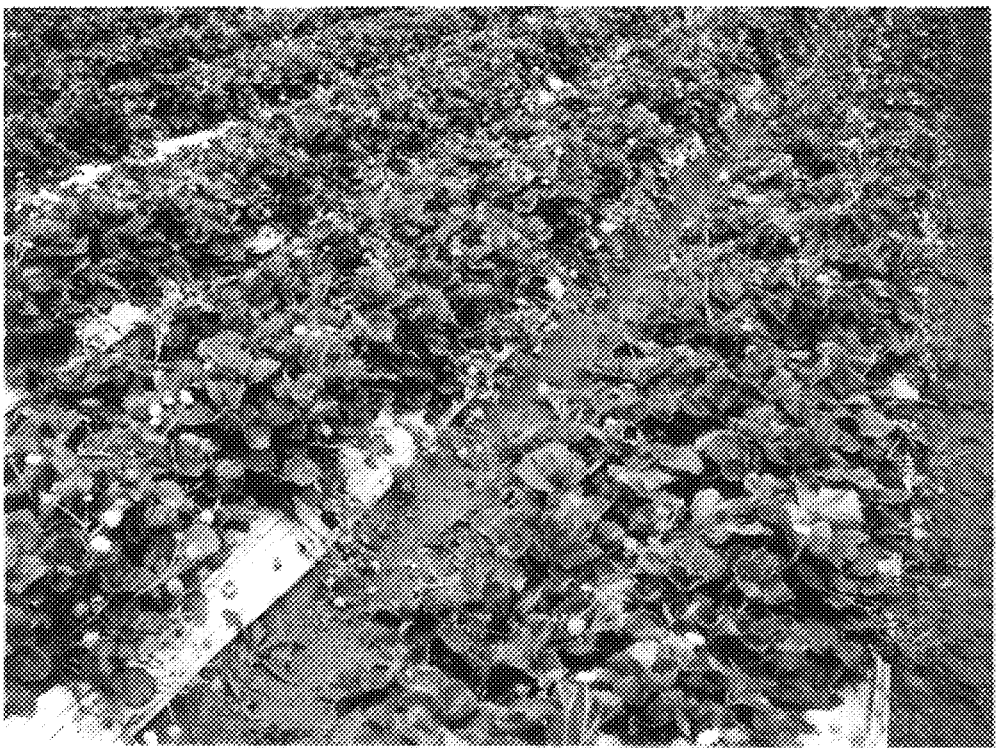

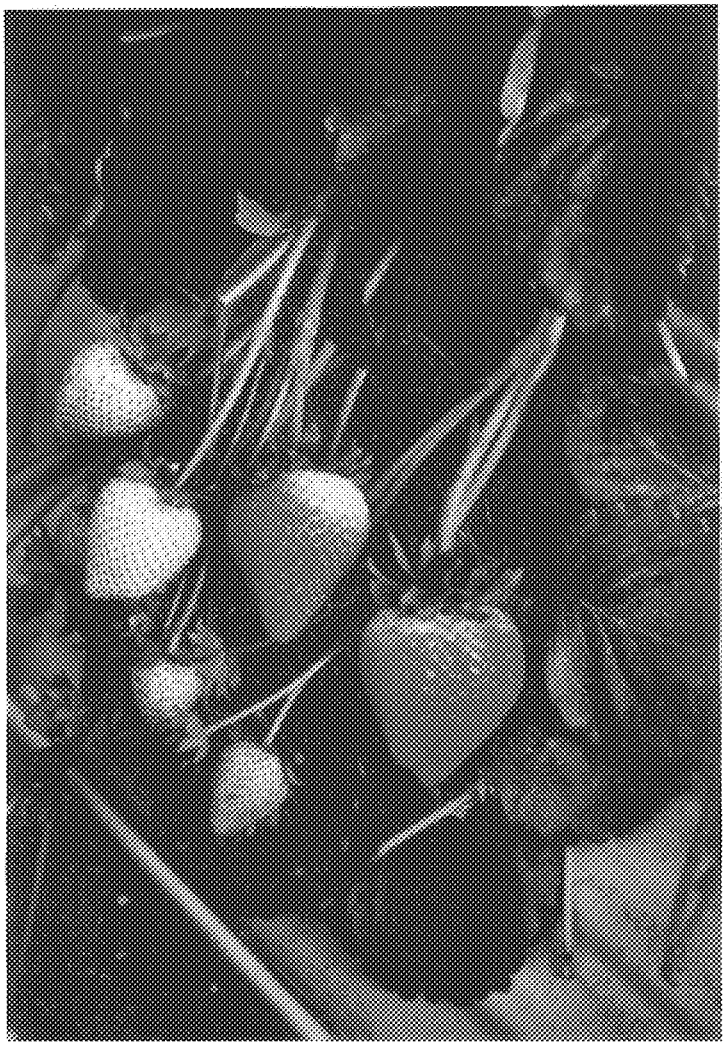

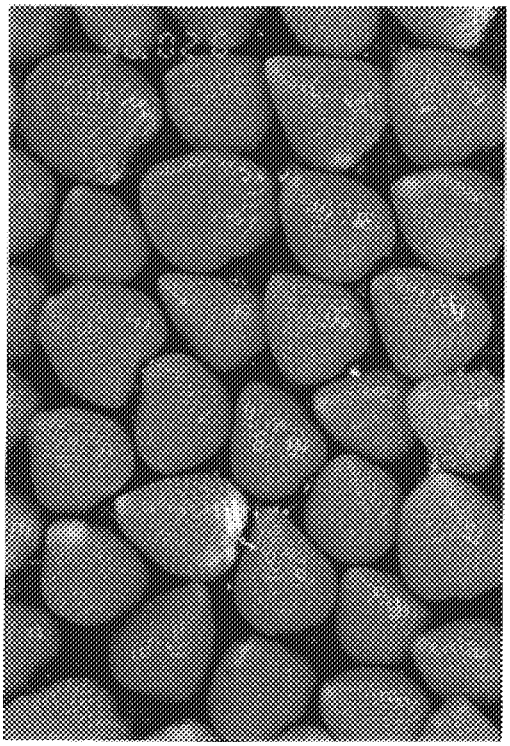
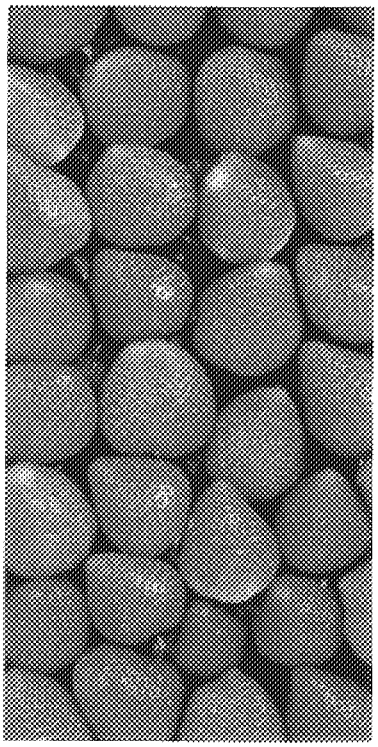

* * * * *